Figure 2:
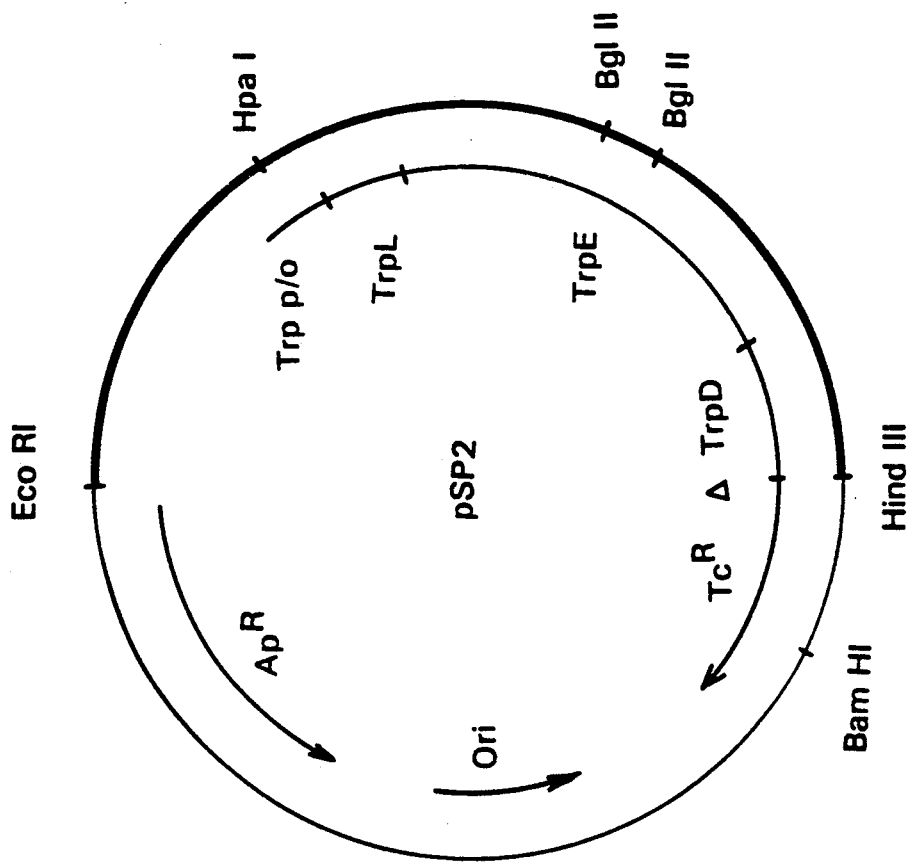

United States Patent [19]

Canosi et al.

[11] Patent Number: 5,268,278
[45] Date of Patent: Dec. 7, 1993

[54] GENETIC EXPRESSION OF SOMATOSTATIN AS HYBRID POLYPEPTIDE

[75] Inventors: Umberto Canosi, Albano; Gabriele De Fazio, Rome; Stefano Villa, Rome; Silva Donini, Rome, all of Italy

[73] Assignee: Istituto Farmacologico Serono S.p.A., Italy

[21] Appl. No.: 193,202

[22] Filed: May 9, 1988

Related U.S. Application Data

[63] Continuation of Ser. No. 717,444, Mar. 29, 1985, abandoned.

[30] Foreign Application Priority Data

Mar. 30, 1984 [IT] Italy ............................. 47976 A/84

[51] Int. Cl.$^5$ ............................................. C12P 21/02
[52] U.S. Cl. ................................. 435/69.7; 435/69.1; 435/69.4; 435/172.3; 435/320.1; 536/23.1; 536/23.4; 536/23.5; 536/23.51; 935/60; 935/73; 935/38; 935/29; 935/13
[58] Field of Search ................ 435/68, 70, 172.3, 320, 435/91, 69.1, 320.1, 69.4, 69.2; 935/47; 536/23.1, 23.5, 23.51, 23.4

[56] References Cited

U.S. PATENT DOCUMENTS 4,431,739  2/1984  Riggs ............................... 435/252.33
4,499,188  2/1985  Konrad et al. ..................... 435/69.51

FOREIGN PATENT DOCUMENTS 0036776  9/1981  European Pat. Off. .
0068719  1/1983  European Pat. Off. .
2052516  6/1983  United Kingdom .

OTHER PUBLICATIONS

Gerhardt et al (eds.) 1981, in *Manual of Methods for General Bacteriology*, Am. Soc. for Microbiol., Washington D.C., pp. 151–178.
Strickberger, M. W. 1976, in *Genetics*, Second Edition Macmillan Publ. Co. New York, pp. 391–434.
Hallewell et al, Gene vol. 9, pp. 27–47 (1980).
Tacon et al, Molec. Gen. Genet. vol. 177 pp. 427–438 (1980).
Das et al., Journal of Biological Chemistry vol. 257 pp. 8795–8798 (1982).
Itakura et al, Science vol. 198 pp. 1056–1063 (1977).

*Primary Examiner*—Christopher S. F. Low
*Attorney, Agent, or Firm*—Ostrolenk, Faber, Gerb & Soffen

[57] ABSTRACT

New plasmid vectors are described, containing the entire Trp regulatory system including promoter, operator, leader and attenuator, and methods for the expression of hybrid polypeptides in E. coli. The hybrid polypeptides can contain the heterologous sequence of somatostatin.

8 Claims, 6 Drawing Sheets

```
         S2              S3                    S4
    1   2   3   4   5   6   7   8   9   10  11  12  13  14
   Met Ala Gly Cys Lys Asn Phe Phe Trp Lys Thr Phe Thr Ser Cys         Stop
                            ↓                       ↓                   ↓
HindIII                                                                           
↓
AGCTTAC ATG GCC↓GGT TGC AAG AAC TTC TTC TGG AAG ACC TTC ACC TCT TGC TAG ATC CTAG
    ATG TAC CGG CCA ACG↑TTC TTG AAG AAG ACC↑TTC TGG AAG TGG↑ACC AGA ACG         BamHI
S1                                                                              
         S8              S7              S6              S5
```

FIG. 1A

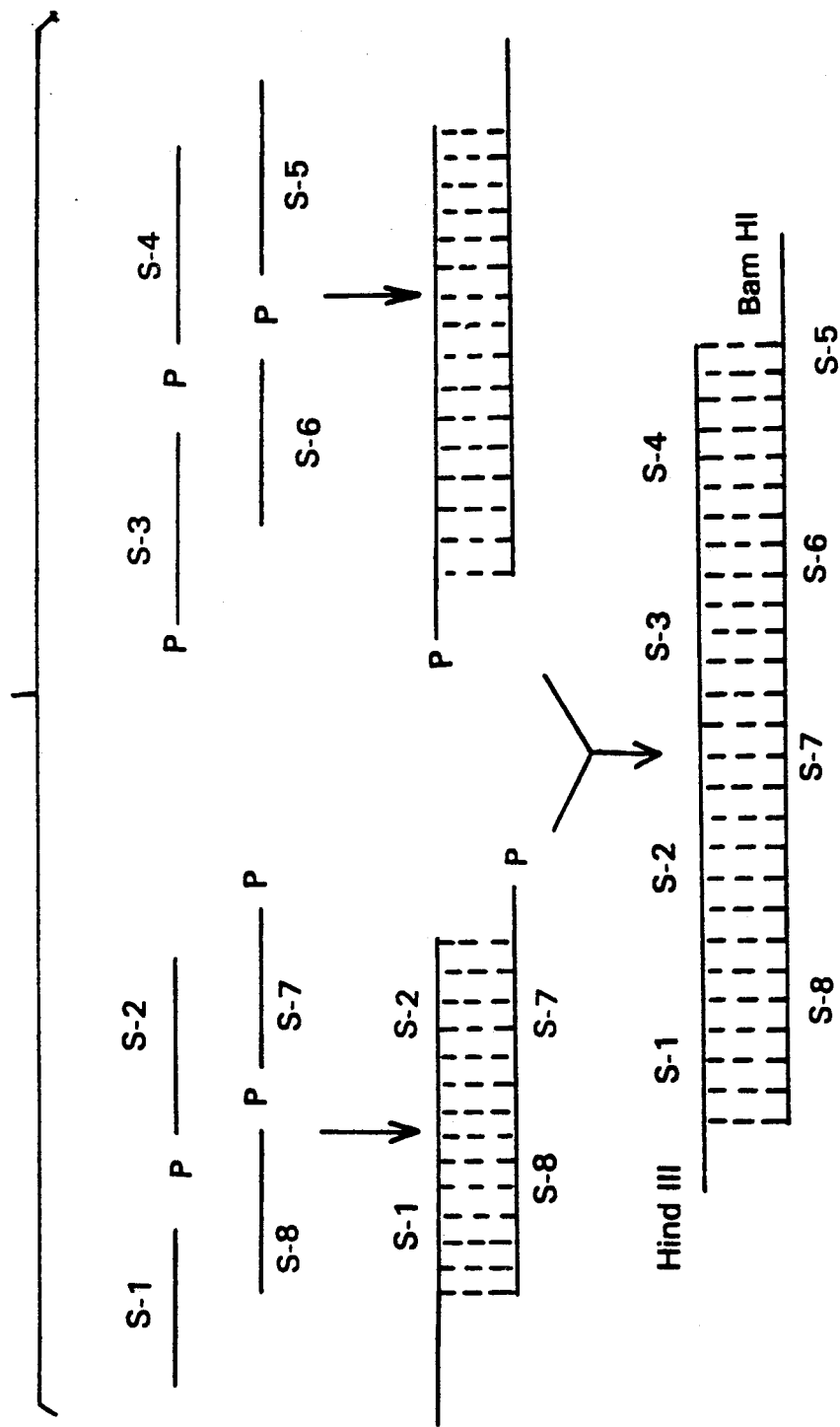

FIG. 5

AMINOACID SEQUENCE OF THE TrpE-SS14 POLYPEPTIDE

MET GLN THR GLN LYS PRO THR LEU GLU LEU LEU THR CYS GLU GLY ALA
TRY ARG ASP ASN PRO THR ALA LEU PHE HIS GLN LEU CYS GLY ASP ARG
PRO ALA THR LEU LEU LEU GLU SER ALA ASP ILE ASP SER LYS ASP ASP
LEU LYS SER LEU LEU LEU VAL ASP SER ALA LEU ARG ILE THR ALA LEU
GLY ASP THR VAL THR ILE GLN ALA LEU SER GLY ASN GLY GLU ALA LEU
LEU ALA LEU LEU ASP ASN ALA LEU PRO ALA GLY VAL GLU SER GLU GLN
SER PRO ASN CYS ARG VAL LEU ARG PHE PRO PRO VAL SER PRO LEU LEU
ASP GLU ASP ALA ARG LEU CYS SER LEU SER VAL PHE ASP ALA PHE ARG
LEU LEU GLN ASN LEU LEU ASN VAL PRO LYS GLU GLU ARG GLU ALA MET
PHE PHE SER GLY LEU PHE SER TYR ASP LEU VAL ALA GLY PHE GLU ASP
LEU PRO GLN LEU SER ALA GLU ASN ASN CYS PRO ASP PHE CYS PHE TYR
LEU ALA GLU THR LEU MET VAL ILE ASP HIS GLN LYS LYS SER THR ARG
ILE GLN ALA SER LEU PHE ALA PRO ASN GLU GLU GLU LYS GLN ARG LEU
THR ALA ARG LEU ASN GLU LEU ARG GLN GLN LEU THR GLU ALA ALA PRO
PRO LEU PRO VAL VAL SER VAL PRO BIS MET ARG CYS GLU CYS ASN GLN
SER ASP GLU GLU PHE GLY GLY VAL VAL ARG LEU LEU GLN LYS ALA ILE
ARG ALA GLY GLU ILE PHE GLN VAL VAL PRO SER ARG ARG PHE SER LEU
PRO CYS PRO SER PRO LEU ALA ALA TYR TYR VAL LEU LYS LYS SER ASN
PRO SER PRO TYR MET PHE PHE MET GLN ASP ASN ASP PHE THR LEU PHE
GLY ALA SER PRO GLU SER SER LEU LYS TYR ASP ALA THR SER ARG GLN
ILE GLU ILE - GLU ARG TYR MET -

```
  1   2   3   4   5   6   7   8   9  10  11  12  13  14
 ALA GLY CYS LYS ASN PHE PHE TRP LYS THR PHE THR SER CYS
```

SOMATOSTATIN 14

GENETIC EXPRESSION OF SOMATOSTATIN AS HYBRID POLYPEPTIDE

This is a continuation of application Ser. No. 717,444 filed on Mar. 29, 1985, now abandoned.

The interest in genetic expression of the peptide somatostatin 14 (SS14) via genetic engineered E. coli/-plasmid system has been alive for several years. The small size of somatostatin permits the design and production of a synthetic somatostatin coding gene.

The amino acid sequence and the effects of somatostatin are described in U.S. Pat. No. 3,904,594.

In Science, Vol. 198 of Dec. 9, 1977, pages 1056 to 1063, Keichi ITAKURA et al reported about the expression in Escherichia coli of a chemically synthesized gene for the hormone somatostatin. In said research a gene for somatostatin, a mammalian peptide hormone, was synthesized by chemical methods. This gene was fused to the Escherichia coli β-galactosidase gene on the plasmid pBR322. Transformation of E. coli with the chimeric plasmid DNA led to the synthesis of a polypeptide including the sequence of amino acids corresponding to somatostatin. In vitro, active somatostatin was specifically cleaved from the large chimeric protein by treatment with cyanogen bromide. European Patent Application No. 1929, analogously reports on the synthesis and cloning of a somatostatin gene within the beta galactosidase gene carried by a plasmid vector. The recombinant plasmid inserted in an E. coli strain via genetic transformation allows the expression of a hybrid protein between beta galactosidase and SS14. Somatostatin 14 was derived from the hybrid protein by CNBr cleavage at the Met residue that joined somatostatin with the rest of the protein. European Patent Application, Publication No. 36776, discloses another E.coli/-plasmid system wherein expression plasmids are provided for the production of heterologous polypeptide products in E.coli, including SS-14.

The vehicles used in said publications have a Trp promoter operator, nucleotides coding for the Trp leader ribosomal binding site and nucleotides encoding translation initiation for the expression of structural genes that encode the amino acid sequence of the heterologous polypeptides. They do not contain a Trp attenuator region or nucleotides coding for the TrpE ribosomal binding site.

The expressed polypeptide is a specifically cleavable, fused protein comprising 6 amino acids of the Trp leader peptide plus the last third of the TrpE polypeptide and the somatostatin 14 peptide. By tryptophan limitation the Trp operator is de-repressed and highly efficient expression of the heterologous polypeptide occurs, unhampered by attenuation because the attenuator region has been deleted from the system. The present invention relates to the production of somatostatin as a hybrid with a plasmid encoded pplypeptide by a strategy based on the use of the E.coli Trp promoter-/operator followed by the Trp leader and attenuator, the TrpE ribosomal binding site, the structural -gene of about the first two thirds of the TrpE polypeptide and the structural gene of the somatostatin 14 peptide, in this order.

An E.coli strain carrying a deletion within the chromosomal Trp operon has been transformed with the expression plasmid according to the invention and the cells grown under mild concentration of tryptophan or of its precursor, indole. These E.coli Trp⁻ cells, when grown in the presence of tryptophan, utilize part of the amino acid present in the medium leaving, after few hours, a Trp concentration sufficiently high to let the cells grow further, and low enough to maintain the Trp operator de-repressed. An operable concentration range is of 3 to 8 μg tryptophan per ml culture medium.

The tryptophan, in the medium, can be replaced by its precursor, indole in a concentration range of about 2 to 6 μg/ml of culture medium. In this case, the E. coli Trp⁻ cells convert the Trp precursor to lip, which is probably almost exclusively utilized for cell growth. The Trp concentration in the milieu remains sufficiently low to maintain the Trp operator de-repressed.

The heterologous polypeptide is continously expressed, up to a maximal level attained after 22-25 hours of growth.

It is particularly surprising that the "strategic" approach on which this invention is based leads to such a good result, while the teaching of the prior art is that the Trp attenuator should not be present.

On the contrary, the contemporaneous presence of the Trp leader and attenuator in the expression plasmid according to this invention permits the optimal Trp concentration to be achieved without changing the culture medium during the complete growth of the cells. The net result is a continous process by which cells are grown while the heterologous polypeptide is expressed. The gene coding for SS14 has been prepared by chemical synthesis as described in FIG. 1A.

The accompanying drawings illustrate aspects of the preferred embodiments of the invention.

FIG. 1.A. - Nucleotide sequence of the chemically synthetized SS14 gene and aminoacids sequence of same SS14. HindIII and BamHI indicate restriction endonuclease recognition sites. The nucleotide sequences within arrows represent the various blocks, from S1 to S8, to be chemically synthetized.

FIG. 1.B. - Shown is the strategy to originate the SS14 coding gene from the various blocks. The oligonucleotide chemical synthesis was performed by the solid phase phosphotriester method using dinucleotides as building blocks and polystyrene as solid support. Most of the codons were selected to be better expressed in E. coli. The complete gene was obtained by ligation of the S-1 to S-8 oligonucleotides with T4 DNA ligase. The SS14 gene was also designated to be in correct reading frame with TrpE gene.

FIG. 2. Restriction map of pSP2 plasmid vector constructed as described in the text. The thin line represents pBR322 DNA, the thick line represents E. coli chromosomal DNA carrying the Trp promoter/operator, the Trp leader sequence (TrpL), the entire TrpE structural gene and partial TrpD structural gene (ΔTrpD). Ap$^R$ and Tc$^R$ indicate the genes that confer resistance to ampicillin and tetracycline respectively. Or i is the origin of replication of this plasmid.

Figure 3:
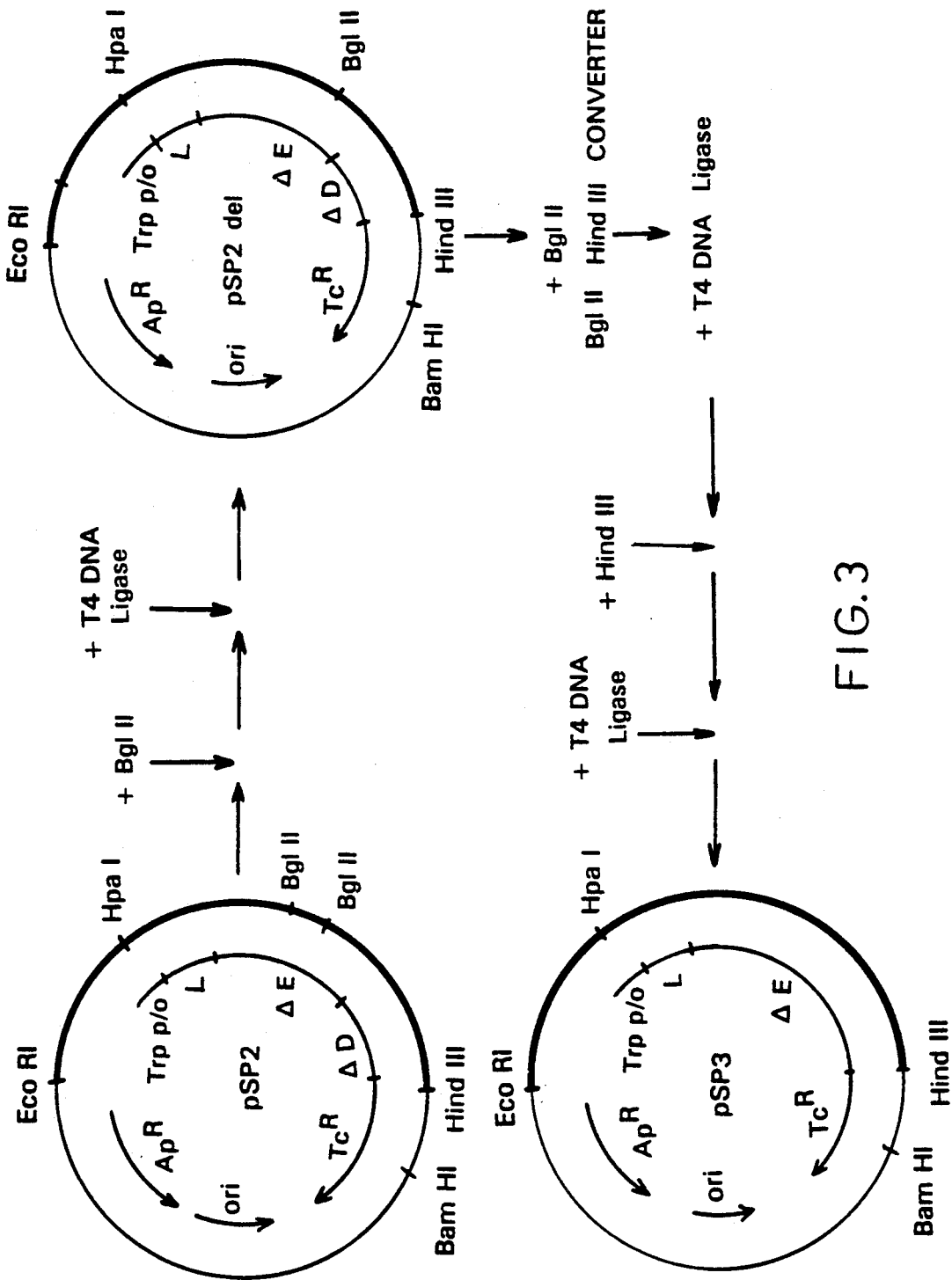

FIG. 3. Construction of pSP2del and pSP3 plasmids performed as described in the text. See description of FIG. 2 ΔE indicates incomplete TrpE structural gene.

Figure 4:
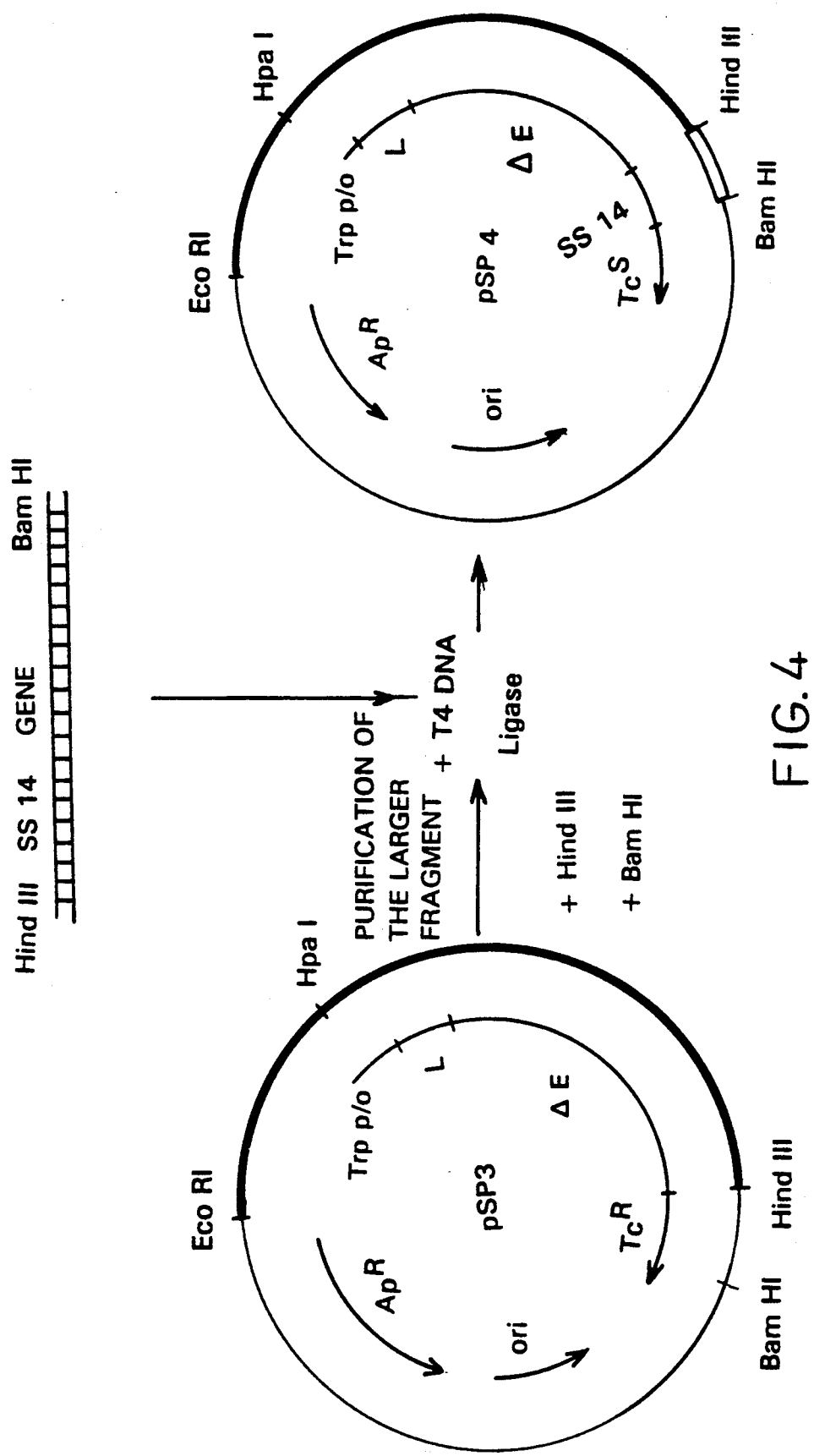

FIG. 4. Cloning of the synthetic DNA molecule coding for SS14 in the pSP3 plasmid vector to form plasmid pSP4. Tc$^S$ indicates sensitivity to tetracycline.

FIG. 5. Aminoacid sequence of the hybrid TrpE-SS14 polypeptide The description which follows illustrates the construction of pSP4 plasmid vector capable to express the hybrid polypeptide TrpE-SS14.

Construction of pSP2 plasmid

The pSP2 plasmid was constructed starting from pBR322 (Bolivar et al, Gene, 2, 95, 1977) and λED10f (Armstrong et al, Science, 196, 172, 1977 and Helsinki et al, in Recombinant Molecules, Tenth Miles International Symposium, Raven Press, 1977, pgg 151–165), which was used as source of E.coli Trp operon DNA, that extends from promoter to TrpD structural gene. pBR322 and λED10f were degraded with EcoRI and HindIII restriction enzymes. The EcoRI-HindIII fragment from λED10f, carrying the Trp operon regulatory functions, the TrpE structural gene and the 5' end of the TrpD structural gene was ligated with the HindIII-EcoRI larger fragment of pBR322 using T4 DNA ligase. The ligation mixture was used to transform E.coli W3110ΔTrpE5 cells (Nichols and Yanofsky, Methods in Enzymology, 101,155,1983). The transformed cells were plated onto minimal medium plates lacking tryptophan. A Trp+clone was used as source of plasmid recombinant DNA pSP2. Cells of this clone were grown and stored in rich medium (i.e. NB, Difco) containing 50 μg/ml of ampicillin (Ap). The restriction map of pSP2 is shown in FIG. 2.

Construction of plasmid pSP2del pSP2 plasmid DNA was degraded with Bgl II endonuclease and the larger fragment was purified by agarose gel electrophoresis and ligated on itself with T4 DNA ligase. The ligation mixture was used to transform W3110ΔTrpE5 cells. Ap$^R$ transformants were selected onto Nutrient Agar (Difco) containing 50 μg/ml Ap. An Ap$^R$ clone was used as source of pSP2del DNA whose restriction map is shown in FIG. 3. The removal of Bgl II fragment from the TrpE structural gene caused the expression of a partial TrpE polypeptide, with loss of its enzymatic activity. The pSP2del carrying W3110 TrpE5 cells must therefore be grown in the presence of tryptophan.

The junction of Bgl II sites in pSP2del creates a new translation stop codon (Nichols et al, J.Mol. Biol. 146, 45–54, 1981).

The TrpE coded by pSP2del (ΔTrpE) is composed of 342 aminoacids against the 520 in the complete TrpE protein coded by pSP2 plasmid (see again FIG. 3).

Construction of pSP3 plasmid pSP2del DNA was cleaved with Bgl II restriction enzyme and then ligated with a Bgl II-HindIII converter (FIG. 3). The nucleotide sequence of the converter was such that the Bgl II sites were not regenerated. The ligation mixture was digested with HindIII, religated on itself and used to transform W3110ΔTrpE cells selecting for Ap$^R$. Some derivative recombinant plasmids appear to have removed the DNA between HindIII of the converter within the TrpE and HindIII that joins with pBR322 DNA (see FIG. 3).

The actual stop codon of the deleted TrpE gene is now a few codons downstream from the HindIII sites. The new TrpE protein is 328 aminoacids long.

Analysis of TrpE and TrpE deleted derivative products

In our preliminary experiments the plasmid containing W3110 TrpE5 cells were grown in LB (Luria-Bertani) medium which contains, per liter aqueous solution, 10 g Bacto-Tryptone, 5 g Bacto-Yeast extract and 10 g NaCl, supplemented with 5 μg/ml ampicillin. In such conditions, the tryptophane is supplied by the medium, and therefore the Trp operon of both chromosome and plasmids is under repression.

For de-repression and expression the cells grown overnight in the LB medium (about 2 OD, 590 nm) are collected by centrifugation and diluted 20 times with SMM (Spizizen Minimal Medium) which contains per liter aqueous solution:

| | |
|---|---|
| $(NH_4)_2SO_4$ | 2 g. |
| $KH_2PO_4$ | 6 g. |
| $K_2HPO_4$ | 14 g |
| Na-Citrate.2H$_2$O | 1 g. |
| $MgSO_4$ | 0.2 g. |

After autoclaving, the following is added:
10 g 40% glucose
Tryptophane 5 μg/ml

The concentration of Trp is enough to allow the growth of the cells and to maintain the Trp operon slightly de-repressed. After 4–5 hours, the TrpE and deleted derivatives were analyzed by incorporation of radioactive amino acids.

Cloning of SS-14 gene and its expression pSP3 DNA was digested with HindIII and BamHI restriction enzymes and the larger fragment was purified from agarose gel. This DNA was added to SS14 synthetic DNA and ligated with T4 DNA ligase (see FIG. 4). The ligation mixture was used to transform W3110ΔTrpE5 cells and Ap$^R$ transformants were selected on plates containing 50 μg/ml ampicillin. The recombinant plasmid containing SS14 gene was isolated and called pSP4.

The nucleotide composition of the SS14 gene allows the production of a hybrid polypeptide containing the partial TrpE and somatostatin. The somatostatin peptide is preceded in the hybrid protein by a methionine which is cleavable by CNBr. The hybrid polypeptide expressed by pSP4 plasmid has the aminoacid sequence shown in FIG. 5 and is conventionally called TrpE-SS14. The first 323 aminoacids represent the first two thirds of the TrpE whereas the four aminoacids delimitated by hyphens are coded by the Bgl II-HindIII converter (see FIG. 3). The converter aminoacids are followed by the 14 specific SS14 aminoacids.

Production of Somatostatin hybrid polypeptide

W3110ΔTrpE (pSP4) cells were grown overnight in 300 ml of minimal medium to which glucose and tryptophan had been added as previously described. This culture (4.3×10$^8$ cells/ml) was diluted in 10 liters of the same medium and the cells were allowed to grow under impeller agitation (300 rpm) and with injection of 3–4 liters of air at 1 Atm per minute. After 22–25 hours of growth, the culture reached an OD (590 nm) of about 2. The cells were harvested and treated with CNBr as described by Itakura et al (Science, 198, 1056–1063, 1977). The somatostatin released was tested by RIA. The average SS14 concentration observed was 300 μg/liter of bacterial culture. An increase up to 400 μg/l of final SS14 concentration was observed when the Trp in the medium was replaced by its precursor indole (3.5 μg/ml). It is believed that the tryptophane derived from the conversion of indole by the bacteria is almost exclusively utilized for the bacterial growth itself. These conditions are therefore ideal to maintain the Trp operon de-repressed. When the W3110 TrpE5 (pSP4) cells are grown in 10 liters of minimal medium, as previously described, containing 3.5 µg/ml of indole, instead of Trp, under impeller agitation and insufflation of only 1 liter of air at 1 Atm per minute, the optical density reached after 22-25 hrs of growth is about 3 at 590 nm. The reduction of the amount of air injected in the medium during the growth results in a 50% increase of bacterial mass without altering the relative concentration of the TrpE-SS14 polypeptide. The concentration of SS14, detected by RIA after CNBr treatment, is about 600 ug/liter of bacterial culture.

The decrease of aereation seems therefore to favour the bacterial growth and, without altering the Trp operon regulatory system, seems to permit the recovery of a higher quantity of bacterial proteins, among which is the TrpE-SS14, from the same volume of bacterial culture.

Characterization of TrpE-SS14 polypeptide

The SS14 concentration detected by RIA was found to be lower than expected by the content in the hybrid polypeptide. It was possible that a particular structural conformation of the TrpE-SS14 protein could be somehow responsible for the observed difference and therefore the properties of the protein were studied as follows. Protein extract of W3110ΔTrpE5 (pSP4) cells was prepared and the Trp-SS14 polypeptide was partially purified by ammonium sulfate precipitation and characterized by Sepharose 4B chromatography. It was thus demonstrated that most of the TrpE-SS14 is recovered from the bacteria as high molecular weight complexes that can be dissolved by reducing agents.

Furthermore such aggregates are determined by both inter and intramolecular disulphide bonds. That such complexes are represented by the TrpE-SS14 polypeptide is demonstrated by an immunoblotting experiment which shows immunoreactivity against SS14 antibodies.

It is concluded that the lower SS14 concentration detected could be due to at least two reasons:

1) Aspecific disulphide bonds can involve the SS14 moiety of the TrpE-SS14 polypeptide, impeding the liberation by CNBr of quantitative immunoreacting SS14 peptide (the cyclic form).
2) TrpE-SS14 aggregates, that could be present into the cells, are less sensitive to CNBr cleavage, leading as a consequence to a decrease in the amount of released cyclic SS14.

E.coli cells W3110ΔTrpE5 containing the plasmids described herein were deposited in the ATCC (Rockville, Md., USA) on Mar. 12, 1985 and identified as follows:

| Strain designation | ATCC No |
|---|---|
| W3110ΔTrpE5 (pSP2) | 53056 |
| W3110ΔTrpE5 (pSP2-del) | 53058 |
| W3110ΔTrpE5 (pSP3) | 53057 |
| W3110ΔTrpE5 (pSP4) | 53055 |

We claim:
1. A method of expressing a polypeptide in Trp⁻ bacterial cells transformed by a vector comprising in sequence the Trp promoter/operator, the Trp leader and attenuator, the TrpE ribosomal binding site, a DNA coding sequence consisting of a sequence coding for about the first two thirds of the TrpE, and the structural gene of the polypeptide, the said expression being under control of the Trp promoter/operator, leader and attenuator wherein the cells are grown in the presence of a tryptophan or indole concentration sufficient to permit cell growth to occur while maintaining the Trp promoter/operator, leader and attenuator derepressed.

2. The method of claim 1 wherein the tryptophan concentration is about 5 micrograms per milliliter of the culture medium.

3. The method of claim 1 wherein the indole concentration is about 3.5 micrograms per milliliter of the culture medium.

4. The method of claim 1 wherein aeration is supplied with the minimum air flow which permits the said cell growth and expression conditions to occur.

5. Method of expressing a hybrid TrpE-Somatostatin polypeptide in E. Coli according to claim 1 wherein the vector comprises, in sequence order, the E. Coli Trp promoter/operator, the Trp leader and attenuator, the TrpE ribosomal binding site, a DNA coding sequence consisting of a sequence coding for about the first two thirds of the TrpE, and the structural gene of the Somatostatin peptide.

6. Method of expressing a hybrid TrpE-Somatostatin polypeptide in E. Coli according to claim 2 wherein the vector comprises, in sequence order, the E. Coli Trp promoter/operator, the Trp leader and attenuator, the TrpE ribosomal binding site, a DNA coding sequence consisting of a sequence coding for about the first two thirds of the TrpE, and the structural gene of the Somatostatin peptide.

7. Method of expressing a hybrid TrpE-Somatostatin polypeptide in E. Coli according to claim 3 wherein the vector comprises, in sequence order, the E. Coli Trp promoter/operator, the Trp leader and attenuator, the TrpE ribosomal binding site, a DNA coding sequence consisting of a sequence coding for about the first two thirds of the TrpE, and the structural gene of the Somatostatin peptide.

8. Method of expressing a hybrid TrpE-Somatostatin polypeptide in E. Coli according to claim 4 wherein the vector comprises, in sequence order, the E. Coli Trp promoter/operator, the Trp leader and attenuator, the TrpE ribosomal binding site, a DNA coding sequence consisting of a sequence coding for about the first two thirds of the TrpE, and the structural gene of the Somatostatin peptide.

* * * * *